(12) United States Patent
Akino (10) Patent No.: US 9,226,715 B2
(45) Date of Patent: Jan. 5, 2016

(54) X-RAY CT APPARATUS

(71) Applicants: Kabushiki Kaisha Toshiba, Tokyo (JP);
Toshiba Medical Systems Corporation,
Otawara-shi (JP)

(72) Inventor: Naruomi Akino, Nasushiobara (JP)

(73) Assignees: Kabushiki Kaisha Toshiba, Tokyo (JP);
Toshiba Medical Systems Corporation,
Otawara-shi (JP)

( * ) Notice: Subject to any disclaimer, the term of this patent is extended or adjusted under 35 U.S.C. 154(b) by 152 days.

(21) Appl. No.: 13/845,951

(22) Filed: Mar. 18, 2013

(65) Prior Publication Data

US 2013/0251093 A1    Sep. 26, 2013

(30) Foreign Application Priority Data

Mar. 22, 2012    (JP) ................. 2012-064692

(51) Int. Cl.
*A61B 6/03* (2006.01)
*A61B 6/00* (2006.01)
*G06T 11/00* (2006.01)

(52) U.S. Cl.
CPC .............. *A61B 6/032* (2013.01); *A61B 6/5205* (2013.01); *G06T 11/006* (2013.01)

(58) Field of Classification Search
CPC .... A61B 6/0306; A61B 6/032; A61B 6/0312; A61B 5/6852; A61B 6/583; A61B 6/027; A61B 2019/5253; A61B 5/04011; A61B 5/0422; A61B 5/055; A61B 5/6855; A61B 5/6856; A61B 5/6857; A61B 6/12; A61B 6/4085; A61B 6/503; A61B 8/0833; A61B 5/0402; A61B 5/04085; A61B 5/0062; A61B 5/0066; A61B 5/0068; A61B 5/0073; A61B 5/0075; A61B 5/0084; A61B 6/5205; A61B 3/102; A61B 3/1225; A61B 6/03; A61B 6/481; A61B 6/487; A61B 6/501; A61B 5/504; A61B 6/507; G01T 11/003; G01N 23/046
USPC ...................................................... 378/4, 19
See application file for complete search history.

(56) References Cited

U.S. PATENT DOCUMENTS

| 7,542,541 | B2 * | 6/2009 | Seamans et al. ................... 378/8 |
| 7,885,371 | B2 * | 2/2011 | Thibault et al. ................... 378/4 |
| 8,005,287 | B2 * | 8/2011 | Grasruck et al. ............. 382/131 |
| 8,135,186 | B2 * | 3/2012 | Bouman et al. ............... 382/128 |
| 8,712,134 | B2 * | 4/2014 | Zamyatin et al. ............. 382/131 |

FOREIGN PATENT DOCUMENTS

| JP | 8-215189 | 8/1996 |
| JP | 2000-175903 | 6/2000 |

* cited by examiner

*Primary Examiner* — Irakli Kiknadze
(74) *Attorney, Agent, or Firm* — Oblon, McClelland, Maier & Neustadt, L.L.P.

(57) ABSTRACT

The X-ray CT apparatus of the embodiment includes an X-ray generating part, an X-ray detector, a reconstruction function setting part, and a reconstruction processor. The X-ray generating part generates X-rays while rotating in a circuital orbit around the subject. The X-ray detector has a plurality of channels and detects the X-rays transmitted through the subject in each channel. The reconstruction function setting part sets the reconstruction function using statistics representing the statistical dispersion of the X-ray amount of the detected X-rays and a predetermined reference reconstruction function. The reconstruction processor carries out the reconstructing the projection data based on the detected X-rays based on the reconstruction function and produces image data.

7 Claims, 10 Drawing Sheets

X-RAY CT APPARATUS

CROSS-REFERENCE TO RELATED APPLICATION

This application is based upon and claims the benefit of priority from Japanese Patent Application No. 2012-064692, filed Mar. 22, 2012; the entire contents of which are incorporated herein by reference.

FIELD

Embodiment(s) of the present invention relate to an X-ray CT apparatus.

BACKGROUND

An X-ray CT (Computed Tomography) system scans subjects (CT imaging) using X-rays. In addition, the X-ray CT apparatus is a system that images the inside of the subject by processing the collected data through a computer.

Specifically, the X-ray CT apparatus radiates X-rays a plurality of times onto the subject from different directions. In addition, the X-ray CT apparatus detects the X-rays transmitted through the subject through an X-ray detector. A plurality of detection data is collected through detection. The collected detection data is A/D converted by a data collector. The detected data is subsequently transmitted to a console device. The console device produces projection data by carrying out preprocessing, etc. on the detected data. Then, the console device carries out reconstruction processing based on the projection data. The console device produces tomographic image data or volume data based on a plurality of tomographic image data by reproduction. The volume data is a data set representing the three-dimensional distribution of CT values corresponding to the three-dimensional regions of the subject.

Reconstruction processing is carried out on the projection data, for example, by providing convolution and back projection using a reconstruction function. The reconstruction function influences by the S/N, granularity, etc. of images (image data) obtained through reconstruction processing.

In addition, regarding the reconstruction function, a single reconstruction function is selected from among a plurality of predetermined reconstruction functions in single CT imaging based on the imaging conditions and experience of the operator and is applied. The imaging conditions include at least one condition from among the imaging site, direction, tube current value, helical pitch, contrast conditions, etc.

DETAILED DESCRIPTION

The X-ray CT apparatus of the embodiment includes an X-ray generating part, an X-ray detector, a reconstruction function setting part, and a reconstruction processor. The X-ray generating part generates X-rays while rotating along a circuital orbit around the subject. The X-ray detector has a plurality of channels and detects the X-rays transmitted through the subject in each channel. The reconstruction function setting part sets a reconstruction function using statistics representing the statistical dispersion of the X-ray amount of the detected X-rays and a predetermined reference reconstruction function. The reconstruction processor carries out reconstructing the projection data based on the detected X-rays based on the reconstruction function and produces image data.

This embodiment is intended to provide an X-ray CT apparatus, medical imaging apparatus that can set the reconstruction function for obtaining a desired image.

First Embodiment

The configuration of the X-ray CT apparatus 1 according to a first embodiment will be described with reference to FIGS. 1 to 7. As "image" and "image data" correspond to each other, these are sometimes equated in the present embodiment.

<Configuration of the Apparatus>

Figure 1:
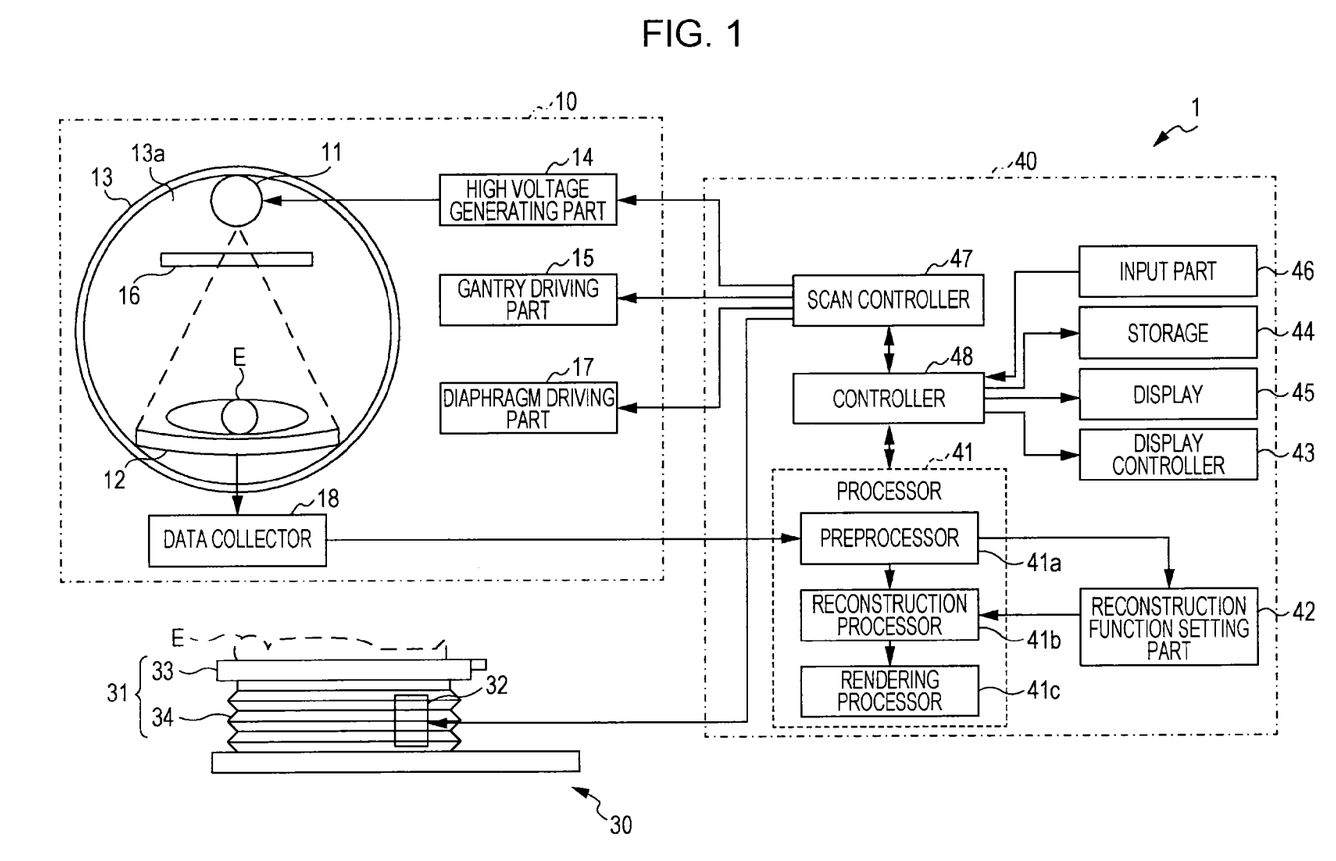
FIG. 1 is a block diagram of the X-ray CT apparatus according to the first embodiment.

As illustrated in FIG. 1, the X-ray CT apparatus 1 comprises a gantry apparatus 10, a couch device 30, and a console device 40.

[Gantry Apparatus]

The gantry apparatus 10 is a device that radiates X-rays onto the subject E and collects the detected data from these X-rays transmitted through the subject E. The gantry apparatus 10 comprises an X-ray generating part 11, an X-ray detector 12, a rotational body 13, a high voltage generating part 14, a gantry driving part 15, an X-ray diaphragm part 16, a diaphragm driving part 17, and a data collector 18.

The X-ray generating part 11 comprises an X-ray tube (not illustrated) for generating X-rays. The produced X-rays are radiated onto the subject E. Further, the X-ray tube is a vacuum tube for generating conical or pyramid-shaped beams.

Figure 2:
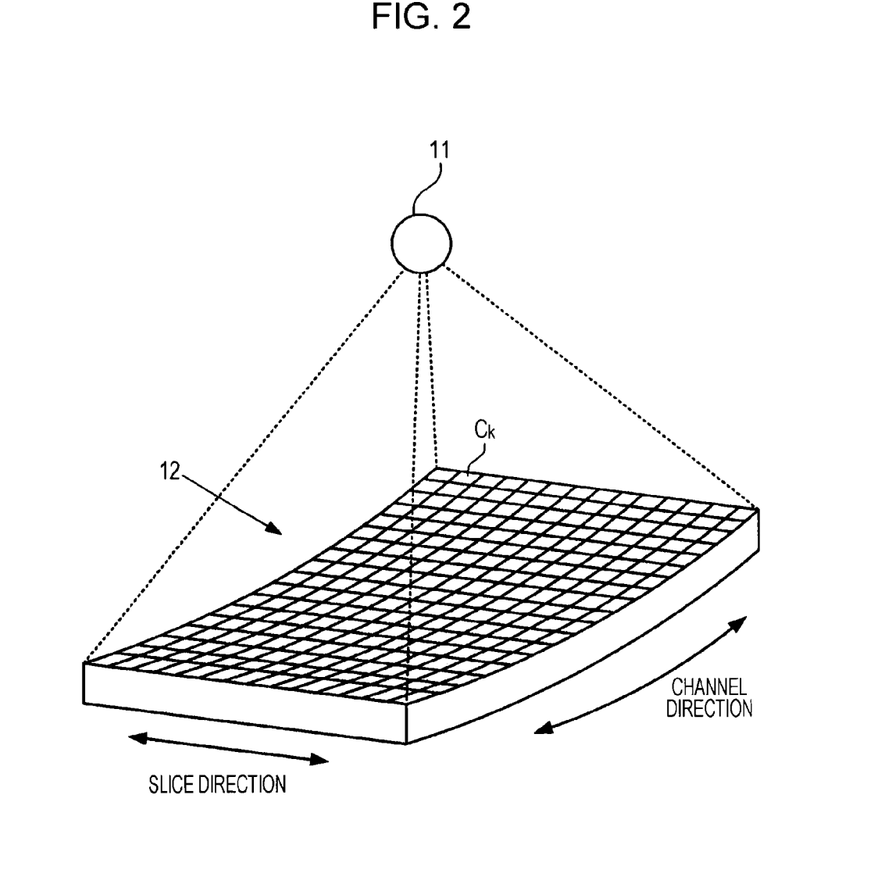
FIG. 2 is a perspective view of an X-ray detector according to the first embodiment.

FIG. 2 is a perspective view of the X-ray detector 12. FIG. 2 only illustrates the X-ray generating part 11 and the X-ray detector 12. The X-ray detector 12 comprises a plurality of X-ray detection elements Ck (k=1 to n). The X-ray detector 12 detects X-ray intensity distribution data (hereinafter, sometimes referred to as "detected data") representing intensity distributions of the X-rays transmitted through the subject E with each X-ray detection element Ck. Further, the X-ray detector 12 outputs the detected data thereof as a current signal. As the X-ray detector 12, for example, a two-dimensional X-ray detector (plane detector) is used, in which a plurality of X-ray detection elements Ck are arranged in two directions orthogonal to each other. These orthogonal two directions comprise the body axial direction of the subject E and the rotational direction of the X-ray generating part 11.

Further, in the present embodiment, each X-ray detection element Ck corresponds to a "channel."

The rotational body 13 is a member that supports the X-ray generating parts 11 and the X-ray detector 12 such that they are opposed through the subject E. The rotational body 13 has an opening 13a, the opening penetrating in the body axial direction. In the gantry apparatus 10, the rotational body 13 is arranged so as to rotate in a circular orbit around the subject E. In other words, the X-ray generating parts 11 and the X-ray detector 12 are arranged so as to be capable of rotating along a circular orbit around the subject E.

The high voltage generating part 14 applies a high voltage to the X-ray generating part 11. The X-ray generating part 11 generates X-rays based on this high voltage. The gantry driving part 15 rotatively drives the rotational body 13. The X-ray diaphragm part 16 has a slit (opening) of a specific width, and adjusts the fan angle (the spread angle in the rotational direction) of the X-rays as well as the cone angle (the spread angle in the body axial direction) of the X-rays radiated from the X-ray generating part 11 by adjusting the width of the slit. The diaphragm driving part 17 drives the X-ray diaphragm part 16 such that the X-rays generated by the X-ray generating part 11 are formed into a predetermined shape.

The data collector 18 (DAS: Data Acquisition System) collects detected data from the X-ray detector 12 (each X-ray detection element). In addition, the data collector 18 converts the collected detected data (current signals) into voltage signals. Moreover, the data collector 18 periodically integrates and amplifies the integrated voltage signals. In addition, the data collector 18 converts them into digital signals. Then, the data collector 18 transmits the detected data converted into digital signals to a console device 40 (a processor 41 (to be described later)).

[Couch Device]

The couch device 30 is a device for mounting and moving the subject E of an imaging object. The couch device 30 comprises a couch 31 and a couch driving part 32. The couch 31 comprises a top board 33 for mounting the subject E thereon and a base 34 for supporting the top board 33. The top board 33 can be moved by the couch driving part 32 in the body axial direction of the subject E and a direction orthogonal to the body axial direction thereof. In other words, the couch driving part 32 can insert or pull the top board 33 on which the subject E mounted into for an opening 13a of the rotational body 13. The base 34 can move the top board 33 vertically (direction orthogonal to the body axial direction of the subject E) using the couch driving part 32.

[Console Device]

The console device 40 is used for manipulating the input into the X-ray CT apparatus 1. In addition, the console device 40 has a function, etc. for reconstructing CT image data (tomographic image data and volume data) representing the inner state of the subject E based on the detected data collected by the gantry apparatus 10. The console device 40 comprises a processor 41, a reconstruction function setting part 42, a display controller 43, a storage 44, a display 45, an input part 46, a scan controller 47, and a controller 48.

The processor 41 carries out various processing with respect to the detected data transmitted from the gantry apparatus 10 (data collector 18). The processor 41 comprises a preprocessor 41a, a reconstruction processor 41b, and a rendering processor 41c.

The preprocessor 41a carries out preprocessing such as logarithmic transformation, offset correction, sensitivity correction, and beam hardening correction, etc. on the detected data detected by the gantry apparatus 10 (X-ray detector 12.) Projection data is produced by way of this preprocessing.

Figure 3:
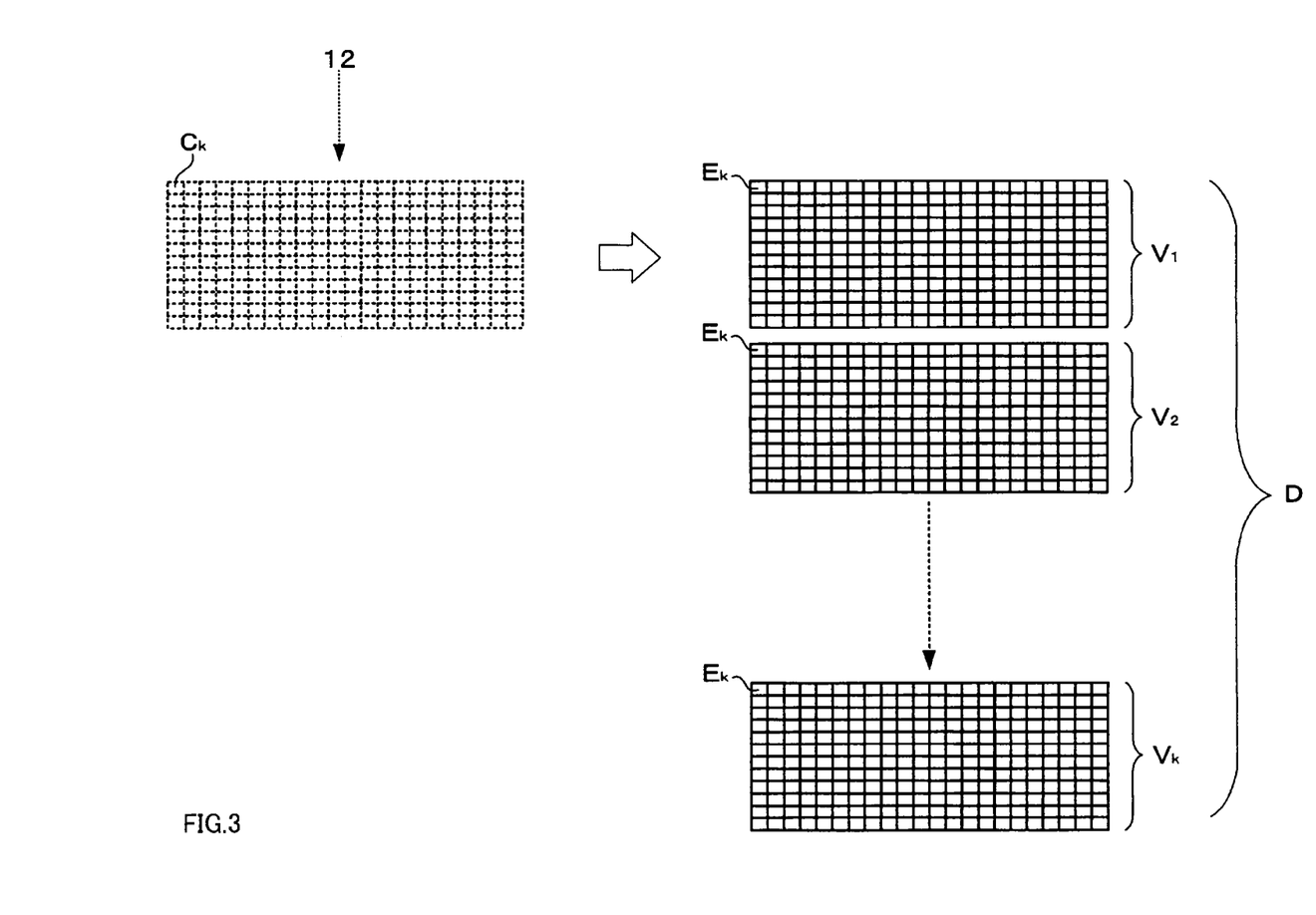
FIG. 3 illustrates projection data obtained by the X-ray CT apparatus according to the first embodiment.

Here, the projection data is produced, for example, based on the detected data detected by CT-imaging the subject E over a wide range. FIG. 3 is a pattern diagram illustrating projection data D obtained by single CT imaging. The projection data D comprises data corresponding to a plurality of views Vk (k=1 to n). One view is the range corresponding to the region of the X-ray detector 12 that detects X-rays when these X-rays are radiated onto the subject E from an arbitrary position in the circuital orbit. Here, the region of the X-ray detector 12 means all channels. Each view Vk has a region Ek (k=1 to n) corresponding to each X-ray detection element Ck (channel) of the X-ray detector 12. In other words, the X-ray detection element Ck of the X-ray detector 12 corresponds to the region Ek in the view Vk on a one-to-one basis.

The reconstruction processor 41b carries out reconstruction processing for the projection data produced by the preprocessor 41a based on the reconstruction function. The projection data is data corresponding to the detected data detected through the X-ray detector 12. In addition, CT image data is produced by this reconstruction processing. The CT image data includes tomographic image data, three-dimensional volume data, etc. For the reconstruction of tomographic image data, for example, a convolution and back projection method is used. Regarding the convolution and back projection method, the projection data obtained through single CT imaging is convolved by the reconstruction function. In addition, according to the convolution and back projection method, a CT image data is produced by back-projecting the projection data. The volume data is produced by interpolating a plurality of reconstructed tomographic image data. In order to reconstruct the volume data, for example, any method such as a cone beam reconstruction method, a multi-slice reconstruction method, an enlarged reconstruction method, etc. can be adopted.

The rendering processor 41c carries out rendering processing for the three-dimensional volume data produced by the reconstruction processor 41b to produce pseudo three-dimensional images. Alternatively MPR images are produced based on the volume data. The "pseudo three-dimensional images" are images for two-dimensionally displaying the three-dimensional configuration of the subject E. The "MPR images" are images indicating the desired cross-section of the subject E. The MPR images include axial images, sagittal images, and coronal images indicating three orthogonal cross-sections and oblique images indicating arbitrary cross-sections, etc.

The reconstruction function setting part 42 weights the reference reconstruction function based on statistics representing the statistical dispersion of the X-ray amount of the X-rays detected by the X-ray detector 12. Thereby, the reconstruction function setting part 42 sets the reconstruction function to be used for reconstruction processing. The reference reconstruction function is set in advance. For example, the reconstruction function setting part 42 sets the reconstruction function $K_{final}(\omega)$ by weighting the reference reconstruction function $K_{base}(\omega)$ based on the variance value that is based on the X-ray amount of detected X-rays. The reference reconstruction function $K_{base}(\omega)$ is a function set based on imaging conditions, etc. For example, a plurality of functions corresponding to the imaging conditions, etc. is stored in the storage 44 as the reference reconstruction function $K_{base}(\omega)$. The reconstruction function setting part 42 reads the corresponding reference reconstruction function $K_{base}(\omega)$ from the storage 44 based on instructions received from the input part 46. In this example, a description will be given provided that the statistic representing dispersion of the X-ray amount of the X-rays detected by the X-ray detector 12 is a variance value.

However, in another example, the standard deviation can be used as the statistic representing the dispersion of the X-ray amount. The following description will be given assuming that the statistic representing dispersion of the X-ray amount is a variance value similar to above. However, this can be replaced with the standard deviation in this embodiment.

Figure 4:
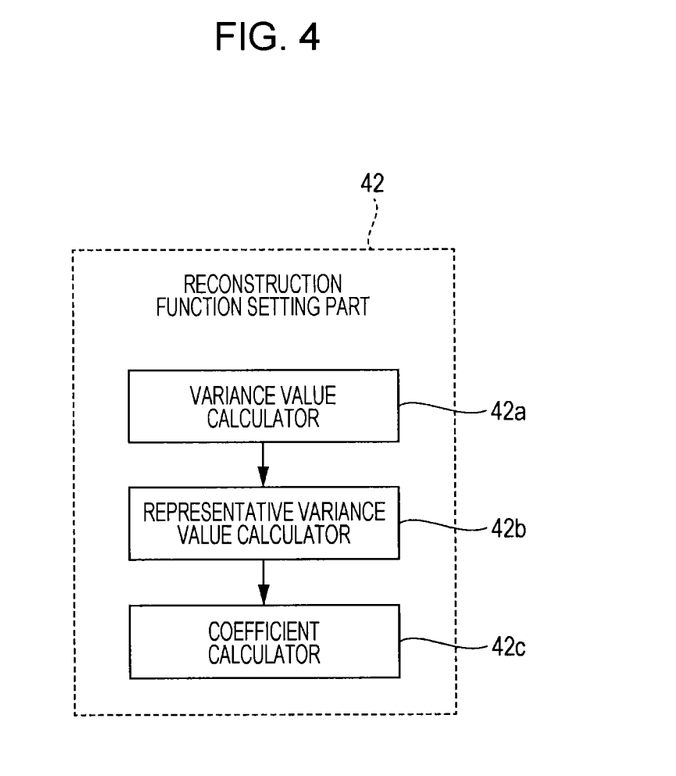
FIG. 4 is a block diagram of the reconstruction function setting part according to the first embodiment.

As illustrated in FIG. 4, the reconstruction function setting part 42 includes a variance value calculator 42a, a representative variance value calculator 42b, and a coefficient calculator 42c.

The variance value calculator 42a calculates the variance value a based on the X-ray amount detected for each channel of the X-ray detector 12 with respect to the projection data. The variance value σ is a value represented by the following formula (1).

[Formula 1]

$$\sigma = (\sqrt{I+Ve})/I^2 \quad (1)$$

A count I is the X-ray amount input into one channel. The variance value Ve is the variance value caused by the circuit noise of the X-ray CT apparatus 1. A value measured in advance for each apparatus is used as the variance value Ve. The variance value σ is a value that varies corresponding to the count I (X-ray amount) in each X-ray detection element Ck (channel). For example, under certain imaging conditions, the statistical dispersion of the X-ray amount when the X-rays are radiated onto a subject E with a large body size is different from the statistical dispersion of when the X-rays are radiated onto a subject E with a slim body size. In other words, the subject E with a large body size has a smaller X-ray amount detected through the X-ray detector 12, that is, a smaller count I. Accordingly, the variance value σ for each channel becomes larger. Thus, the variance value σ is a value reflecting the body size, the site, etc. of the subject E.

In addition, as described above, the X-ray detection element Ck (channel) corresponds to the region Ek on a one-to-one basis. In the present embodiment, the variance value calculator 42a calculates the variance value σk (k=1 to n) for each region Ek of the view Vk.

The representative variance value calculator 42b calculates the representative variance value σT based on a plurality of variance values σ calculated by the variance value calculator 42a. The representative variance value σT is a variance value to be used for obtaining the weight coefficient (to be described later). The representative variance value calculator 42b calculates the representative variance value σT, for example, by averaging a plurality of variance values. Alternatively, the representative variance value calculator 42b can also calculate the median value, the maximum value, the minimum value, etc. of a plurality of variance values as the representative variance value σT.

In addition, in the present embodiment, the representative variance value calculator 42b calculates single representative variance values σT based on all the variance values σk for each region Ek of views Vk calculated by the variance value calculator 42a (namely, all variance values in the projection data D). For example, when the X-rays are radiated onto various subjects, the variance value σ for each channel is larger when the X-rays are radiated onto a subject E of a large body size than when the X-rays are radiated onto a subject E of a slim body size. As a result, the representative variance value σT obtained by averaging these variance values is also larger when the X-rays are radiated onto the subject E of a large body size.

The coefficient calculator 42c calculates a weight coefficient w (ω) based on the representative variance value σ T.

The weight coefficient w (ω) is the coefficient to be used for setting the optimized reconstruction function $K_{final}$ (ω) with respect to the projection data D. In addition, the weight coefficient w (ω) is a coefficient to be used for adjusting the S/N and granularity of the CT image based on the projection data. The reconstruction function setting part 42 sets the reconstruction function $K_{final}$(ω) by weighting the reference reconstruction function $K_{base}$ (ω) using the weight coefficient w (ω). The reconstruction function $K_{final}$ (ω) is the parameter that finally determines the spatial resolution and image noises of the CT image.

A specific method of calculating the weight coefficient w (ω) and setting the reconstruction function $K_{final}$ (ω) will be described.

The first method of calculating the weight coefficient w (ω) includes a method of setting an arbitrary setting parameter for every CT imaging. In this case, the coefficient calculator 42c calculates the weight coefficient w (ω), for example, using the following formula (2).

[Formula 2]

$$w(\omega) = \text{scale} \cdot \sigma_T \cdot \frac{1}{1 + \exp(\omega_{TH} - \omega/\text{slope})} \quad (2)$$

Wherein, "ω" is a value indicating the spatial frequency (virtual frequency) of the reference reconstruction function $K_{base}$ (ω). "ωTH" is a value indicating the specific spatial frequency in the reference reconstruction function $K_{base}$ (ω). "scale" is a value indicating the range of the spatial frequency using the reference reconstruction function $K_{base}$ (ω) based on ωTH. "slope" is a value indicating the slope of the reference reconstruction function $K_{base}$ (ω) in the range of the scale. ωTH and slope are values adjusting the S/N and granularity of the image. Scale is a value for adjusting the granularity of the image. Each of ωTH, scale, and slope are examples of set parameters, and are values that can be arbitrarily set according to the body size, imaging site, etc. of the subject E. The set parameter is set based on the instructions received from the input part 46.

For example, when the X-rays are radiated onto various subjects, the X-ray amount detected through the X-ray detector 12 (signal amount of the detected data) is smaller when the subject E has a large body size than when the subject E has a slim body size. Therefore, the S/N is worse when the CT image of the subject has a large body size than when the CT image of the subject has a slim body size. In other words, the noise is larger for the signal amount of the detected data when the CT image of the subject has a large body size. Therefore, the operator sets the set parameters according to the body size of the subject E. The coefficient calculator 42c calculates the weight coefficient w (ω) that reduces noise based on this set parameter and the representative variance value σT.

The reconstruction function setting part 42 sets the reconstruction function $K_{final}$ (ω) using the following formula (3) using the weight coefficient w (ω).

[Formula 3]

$$K_{final}(\omega) = K_{base}(\omega) + K_{base}(\omega) \cdot w(\omega) \quad (3)$$

Figure 5A:
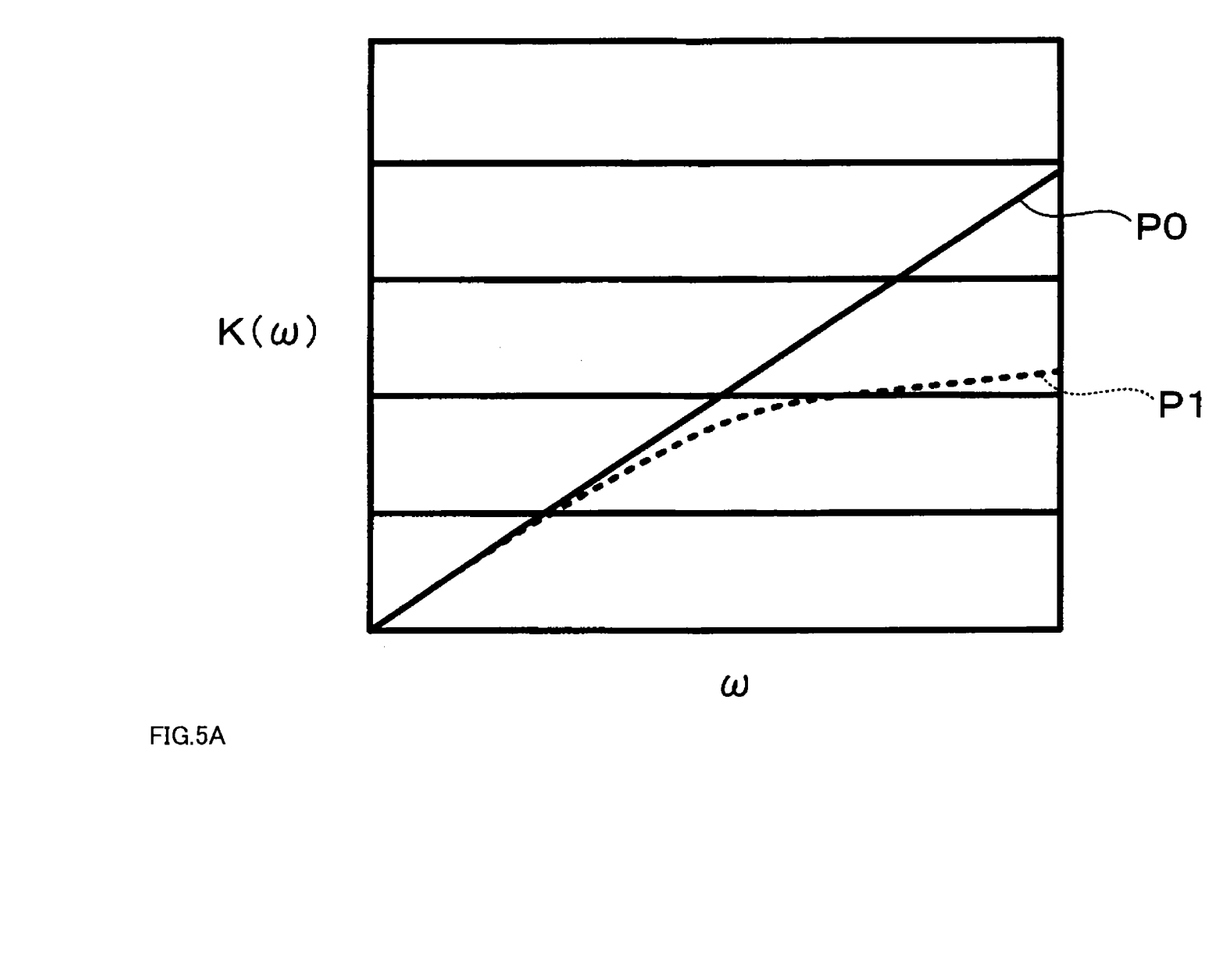
FIG. 5A illustrates a profile of the reconstruction function according to the first embodiment.
Figure 5B:
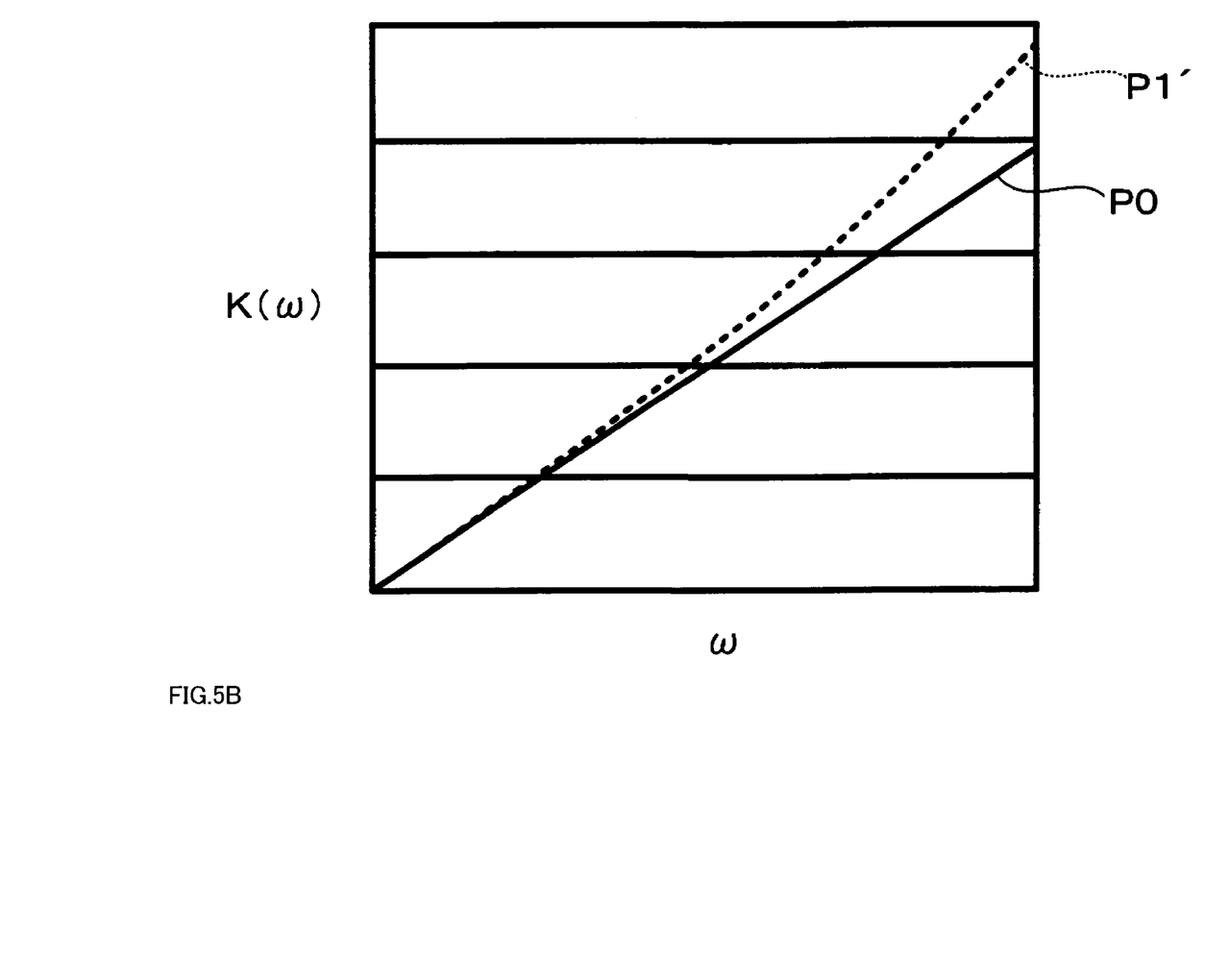
FIG. 5B illustrates a profile of the reconstruction function according to the first embodiment.

FIG. 5A and FIG. 5B illustrate profiles of the reference reconstruction function $K_{base}$ (ω) and the set reconstruction function $K_{final}$ (ω). FIG. 5A illustrates a profile P0 of the reference reconstruction function $K_{base}$ (ω). Further, FIG. 5A illustrates a profile P1 of the reconstruction function $K_{final}$ (ω) based on the weight coefficient w (ω) calculated when the representative variance value σT is 1 in the set parameter of "ωTH=0.543, slope=0.128, scale=−0.5".

In FIG. 5A, the profile P1 is located below the profile P0. This means that the sensitivity on the part with a high spatial frequency of the profile P1 is lower than that of the profile P0. Here, the reconstruction function $K_{final}(\omega)$ corresponds with the profile P1, and the reference reconstruction function $K_{base}(\omega)$ corresponds with the profile P0. In other words, regarding reconstruction processing, weighting on the part with a high spatial frequency is smaller when the reconstruction function $K_{final}(\omega)$ is used than when the reference reconstruction function $K_{base}(\omega)$ is used. In other words, the noise in the projection data is reduced when the reconstruction function $K_{final}(\omega)$ is used. Accordingly, in the case of carrying out reconstruction processing using the reconstruction function $K_{final}(\omega)$, the S/N of the CT image based on the projection data is improved. For example, even if X-rays of the same amount are radiated, the X-ray amount to be detected is small when the subject E has a large body size. In other words, when subjects of different body sizes are imaged under the same imaging conditions, and the CT images are obtained respectively by carrying out reconstruction processing with the reference reconstruction function $K_{base}(\omega)$, the S/N of the image of the large subject is worse than that of the image of the slim subject. In the image of the subject having a large body size, the noise is larger than the signal amount of detected data. Therefore, the reconstruction processor 41b reconstructs for the projection data of the subject E having a large body size using the reconstruction function $K_{final}(\omega)$. As a result, it is possible to obtain an image with improved S/N, namely, an image with a fixed S/N regardless of the body size of the subject E.

On the other hand, smooth filtering may be carried out on the projection data before reconstruction processing is carried out in order to reduce noise. It is possible that the granularity of the CT image based on this projection data may be worse than that of the CT image with no smooth filtering carried out.

In this case, the coefficient calculator 42c calculates the weight coefficient $w(\omega)$ using a scale changed from −0.5 to +0.5 in the above-described set parameters. FIG. 5B illustrates a profile P1 of the reconstruction function $K_{final}(\omega)$ obtained by weighting the reference reconstruction function $K_{base}(\omega)$ with this weight coefficient $w(\omega)$, and illustrates the profile P0 of the reference reconstruction function $K_{base}(\omega)$. In FIG. 5B, the profile P1' is located above the profile P0. This means that the sensitivity on the part with a high spatial frequency of the profile P1' is higher than that of the profile P0. In other words, this means that, regarding reconstruction processing, weighting on the part with a high spatial frequency is larger when the reconstruction function $K_{final}(\omega)$ corresponding to the profile P1 is used than when the reference reconstruction function $K_{base}(\omega)$ corresponding to the profile P0 is used. Accordingly, since the noise of the projection data is emphasized, it is possible to improve the granularity of the CT image. Here, the frequency component of the noise to be emphasized is different from the frequency component of the noise to be reduced through smooth filtering.

Thus, it is possible to set a reconstruction function capable of obtaining a desired CT image by adjusting an arbitrary set parameter regarding the variance value based on the X-ray amount.

Figure 6A:
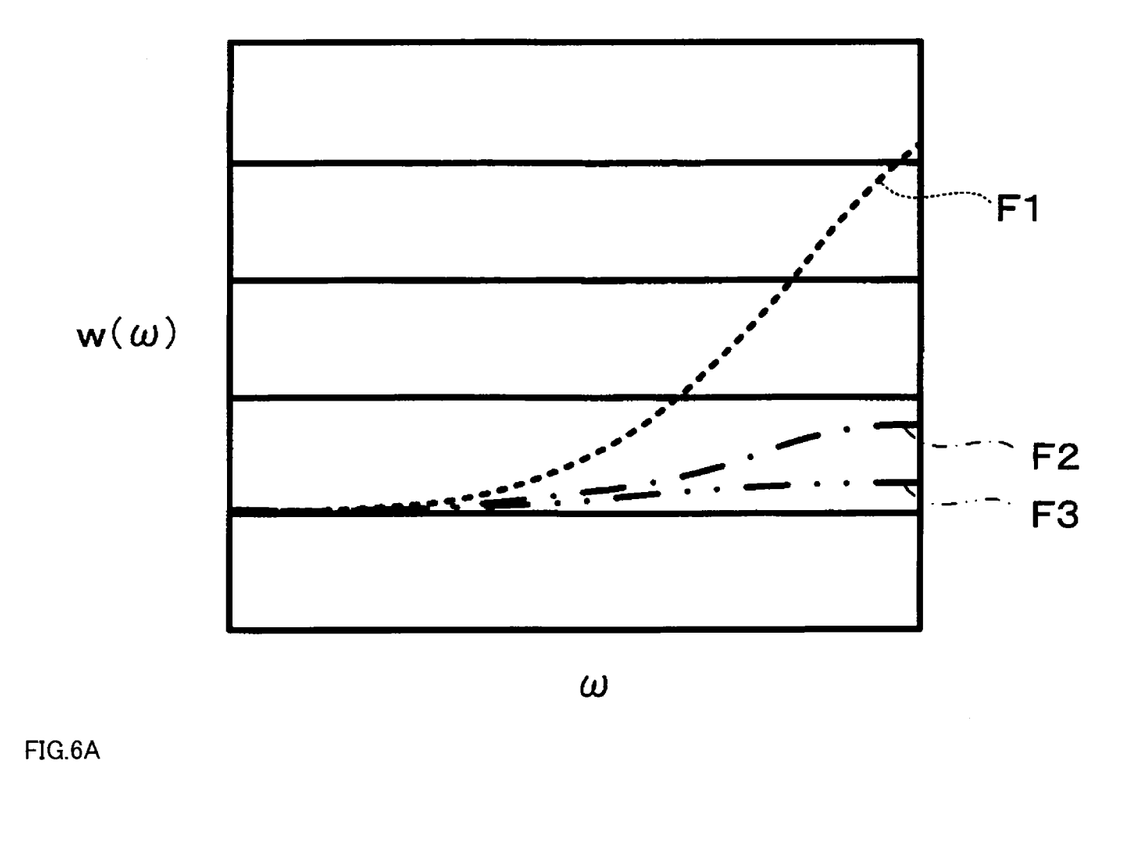
FIG. 6A illustrates a profile of the weight coefficient according to the first embodiment.
Figure 6B:
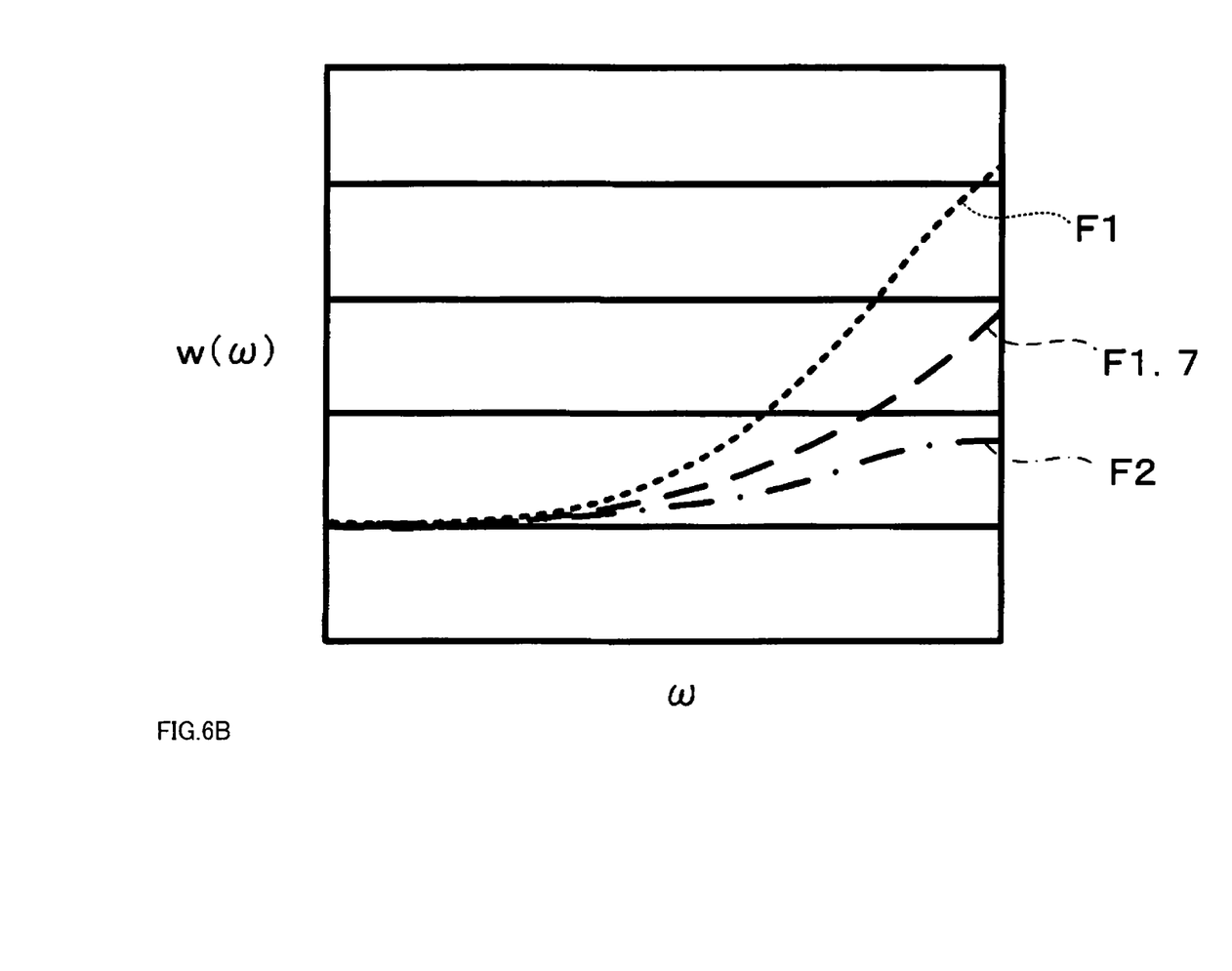
FIG. 6B illustrates a profile of the weight coefficient according to the first embodiment.

According to the second method of calculating the weight coefficient $w(\omega)$, setting several types of weight coefficients corresponding to several types of representative variance values in advance, these weight coefficients are stored in the storage 44, etc. as a table. For example, in the example of FIG. 6A, σT=1 to 3 are set as representative variance values, and w1 (ω) to w3 (ω) are set as weight coefficients. FIG. 6A illustrates profiles F1 to F3 of the weight coefficients w1 (ω) to w3 (ω). For example, the coefficient calculator 42c compares a representative variance value σT=2 calculated by the representative variance value calculator 42b with the stored representative variance values σT=1 to 3. In addition, as a result of this comparison, the coefficient calculator 42c obtains the weight coefficient w2 (ω) corresponding to the coincident representative variance value σT=2. In addition, the coefficient calculator 42c defines this obtained weight coefficient w2 (ω) as the weight coefficient to be used for setting the reconstruction function $K_{final}(\omega)$. Further, similar to the case in which the representative variance value σT is calculated as 1.7, no coincident representative variance value may exist. In such a case, the coefficient calculator 42c refers to profiles F1 and F2 of the weight coefficients w1 (ω) and w2 (ω) in representative variance values σT=1 and 2 close to the calculated representative variance value in the stored representative variance values σT=1 to 3. In addition, the coefficient calculator 42c calculates the weight coefficient w (ω) (profile F1.7) when the representative variance value is 1.7 by linearly interpolating values of respective ω in the profiles F1 and F2 (refer to FIG. 6B.). The reconstruction function setting part 42 sets the reconstruction function $K_{final}(\omega)$ capable of obtaining a desired CT image by weighting the reference reconstruction function $K_{base}(\omega)$ with the calculated weight coefficient w (ω).

The display controller 43 carries out various controls regarding image display. For example, the display controller 43 controls the display 45 so as to display images based on the image data produced by the reconstruction processor 41b.

The storage 44 comprises a semiconductor storing device such as RAM, ROM, etc. The storage 44 stores the detected data, the projection data, the CT mage data, the above-described table, the reference reconstruction function $K_{base}(\omega)$, the reconstruction function $K_{final}(\omega)$, the weight coefficient w (ω), or Formula 1 to 3, etc. that has been provided by reconstruction processing, other than the position at which the insertion route is set.

The display 45 comprises an arbitrary display device such as an LCD (Liquid Crystal Display) and a CRT (Cathode Ray Tube) display, etc. For example, the MPR images acquired by rendering the volume data are displayed on the display 45.

The input part 46 is used as an input device that carries out various operations on the console device 40. The input part 46 is composed of, for example, a keyboard, a mouse, a track ball, a joystick, etc. In addition, it is also possible to use a GUI (Graphical User Interface) displayed on the display 45 as the input part 46.

The scan controller 47 controls various operations regarding X-ray scanning. For example, the scan controller 47 controls the high voltage generating part 14 so as to apply a high voltage to the X-ray generating part 11. The scan controller 47 controls the gantry driving part 15 so as to drive the rotational body 13 rotatively. The scan controller 47 controls the diaphragm driving part 17 so as to operate the X-ray diaphragm part 16. The scan controller 47 controls the bed driving part 32 so as to move the couch 31.

The controller 48 carries out overall control of the X-ray CT apparatus 1 by controlling operations of the gantry apparatus 10, the couch device 30, and the console device 40. For example, the controller 48 makes the gantry apparatus 10 carry out preliminary scanning as well as main scanning by controlling the scan controller 47. Thereby, the controller 48 controls the gantry apparatus 10 to collect the detected data. In addition, the controller 48 controls the processor 41 to carry out various processing (preprocessing, reconstruction processing, etc.) on the detected data. In addition, the controller 48 controls the display controller 43 so as to display the images based on the CT image data on the display 45, etc. stored in the storage 44.

<Operation>

Figure 7:
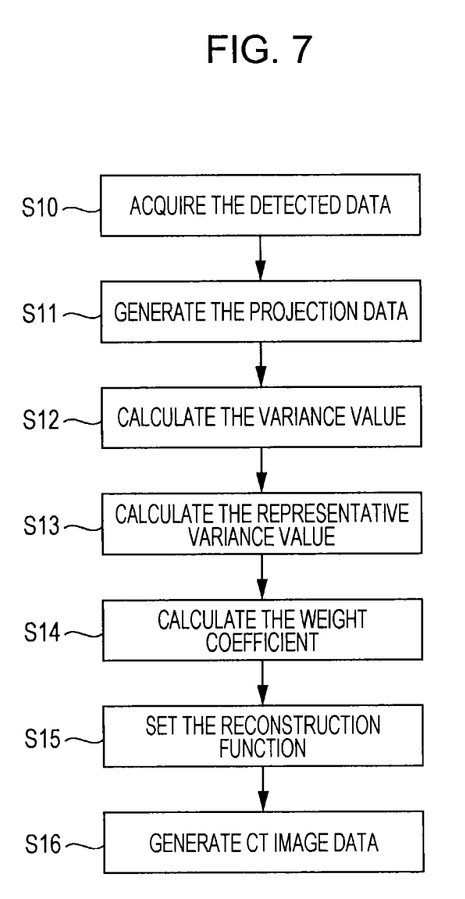
FIG. 7 is a flowchart illustrating the summary of the operation of the X-ray CT apparatus according to the first embodiment.

Next, with reference to FIG. 7, the operation of the X-ray CT apparatus 1 according to the present embodiment will be described.

At first, the X-ray generating part 11 radiates X-rays onto the subject E. The X-ray detector 12 detects the X-rays transmitted through the subject E, and acquires the detected data (S10). The detected data detected by the X-ray detector 12 is collected by the data collector 18. Further, the detected data is transmitted to the processor 41 (preprocessor 41*a*).

The preprocessor 41*a* carries out preprocessing such as logarithmic transformation processing, offset correction, sensitivity correction, and beam hardening correction on the detected data acquired in S10. Thereby, projection data is produced (S11). The produced projection data is transmitted to the reconstruction processor 41*b* and the reconstruction function setting part 42 (variance value calculator 42*a*) based on the control by the controller 48.

The variance value calculator 42*a* calculates the variance value a for each corresponding channel based on the projection data produced in S11 (S12). The calculated variance value σ is transmitted to the representative variance value calculator 42*b*.

The representative variance value calculator 42*b* calculates the representative variance value σT by averaging all variance values calculated in S12 (S13). The calculated representative variance value σT is transmitted to the coefficient calculator 42*c*.

The coefficient calculator 42*c* calculates the weight coefficient w (ω) based on the representative variance value σT calculated in S13 and an arbitrary set parameter (S14).

The reconstruction function setting part 42 sets the reconstruction function $K_{final}(\omega)$ using the weight coefficient w (ω) calculated in S14 and the reference reconstruction function $K_{base}(\omega)$ set in advance (S15). The set reconstruction function $K_{final}(\omega)$ is transmitted to the reconstruction processor 41*b*.

The reconstruction processor 41*b* convolves the projection data with the reconstruction function $K_{final}(\omega)$ set in S15 and back-projects this projection data. Thereby, the reconstruction processor 41*b* produces CT image data (S16). The display controller 43 can display the CT image based on the produced CT image data on the display 45. This CT image is an image reconstructed by the optimum reconstruction function set using the variance value and the reference reconstruction function. Accordingly, a desired CT image such as an image with a good S/N, an image with good granularity, etc. is displayed.

Further, the processor 41, the reconstruction function setting part 42, the display controller 43, the scan controller 47, and the controller 48 may be configured by, for example, a processing apparatus (not illustrated) such as CPU (Central Processing Unit), GPU (Graphic Processing Unit), or ASIC (Application Specific Integrated Circuit), and a storing device (not illustrated) such as ROM (Read Only Memory), RAM (Random Access Memory), or HDD (Hard Disc Drive). Processing programs for carrying out the functions of the processor 41 are stored in the storing device. In addition, a program for setting a reconstruction function to execute the function of the reconstruction function setting part 42 is stored in the storing device. Moreover, the display control programs carrying out the functions of the display controller 43 are stored in the storing device. Moreover, the scan control programs for carrying out the functions of the scan controller 47 are stored in the storing device. Moreover, the control programs for carrying out the functions of the controller 48 are stored in the storing device. A processing device such as a CPU carries out the function of respective parts by carrying out respective programs stored in the storing device.

<Operation and Effect>

The operation and effect of the present embodiment will be described.

The X-ray CT apparatus 1 of the present embodiment includes an X-ray generating part 11, a X-ray detector 12, a reconstruction function setting part 42, and a reconstruction processor 41*b*. The X-ray generating part 11 generates X-rays while rotating in a circuital orbit around the subject E. The X-ray detector 12 has a plurality of channels and detects the X-rays transmitted through the subject E in each channel. The reconstruction function setting part 42 weights the reference reconstruction function set in advance based on the statistics representing statistical dispersion of the X-ray amount of the detected X-rays. Thereby, the reconstruction processing function setting part 42 sets the reconstruction function used for reconstruction processing. For example, the reconstruction function setting part 42 sets the reconstruction function $K_{final}(\omega)$ by weighting the reference reconstruction function $K_{base}(\omega)$ set in advance based on a variance value based on the X-ray amount of the detected X-rays. The reconstruction processor 41*b* carries out reconstruction processing on the projection data based on the detected X-rays based on the reconstruction function $K_{final}(\omega)$, and produces image data.

Specifically, the reconstruction function setting part 42 of the present embodiment includes a variance value calculator 42*a*, a representative variance value calculator 42*b*, and a coefficient calculator 42*c*. The variance calculator 42*a* calculates the variance value σ based on the X-ray amount detected for each channel of the X-ray detector 12 regarding the projection data D. The representative variance value calculator 42*b* calculates the representative variance value σT based on the plurality of calculated variance values σ. In the present embodiment, the representative variance value σT is calculated based on all variance values σ calculated by the variance value calculator 42*a*. The coefficient calculator 42*c* calculates the weight coefficient w (ω) based on the representative variance value σT. Then, the reconstruction function setting part 42 sets the reconstruction function $K_{final}(\omega)$ by weighting the reference reconstruction function $K_{base}(\omega)$ with the weight coefficient w (ω).

Thus, the coefficient calculator 42*c* calculates the weight coefficient w (ω) based on the variance value of the projection data (representative variance). Then, the reconstruction function setting part sets the reconstruction function $K_{final}(\omega)$ by weighting the reference reconstruction function $K_{base}(\omega)$ using the weight coefficient w (ω). For example, the small X-ray amount is detected regarding the subject E having a large body size. Accordingly, the coefficient calculator 42*c* calculates a weight coefficient w (ω) in which weighting on the part with a high spatial frequency is smaller than the reference reconstruction function $K_{base}(\omega)$ based on the representative variance value σT. The reconstruction processor 41*b* reconstructs the projection data using the reconstruction function $K_{final}(\omega)$ set based on the present weight coefficient w (ω). Consequently, the CT image data obtained by reconstruction is an image having a good S/N with the noise reduced. In other words, the X-ray CT apparatus 1 of the present embodiment makes it possible to set the reconstruction function for obtaining a desired image.

Second Embodiment

Next, the configuration of the X-ray CT apparatus 1 according to the second embodiment will be described. In the present embodiment, an example in which the reconstruction function $K_{final}(\omega)$ is set for each specific range will be described. Further, detailed explanations of the configuration, etc. identical with the first embodiment may be omitted. In addition, statistics representing the variance value of the X-ray amount of the X-ray will be described as a variance value in the following description similar to the first embodiment. However, in another example, it is possible to use the standard deviation as the statistic representing statistical dispersion of the present X-ray amount. Accordingly, it is possible to replace the variance value with the standard deviation in the following description as well.

The variance value calculator 42a in the present embodiment divides the projection data D for each specific range, and calculates the variance value for each specific range (variance values σ1 to σn of the channel). The specific range is, for example, a range for each view, or a site of the subject E (head, breast, abdomen, etc.). Hereinafter, the case in which the specific range is the range for each view (views V1 to Vn) will be described. Further, the specific range may be the range of an entire circumference (of a single rotation) in the circuital orbit of the rotational body 13. In other word, the specific range includes from 1 view to view at the time when a single rotation have passed in the circuital orbit of the X-ray generating part.

In the present embodiment, the representative variance value calculator 42b calculates the representative variance value for each specific range based on the variance value for each specific range.

Specifically, the representative variance value calculator 42b calculates the representative variance value σT1 in the view V1 by averaging variance values σ1 to σn of the channel corresponding to the region E1 of the view V1. Further, the region En is a region corresponding to the channel of the X-ray detector 12. Similarly, the representative variance value calculator 42b calculates the representative variance value σTn in the view Vn by averaging variance values σ1 to σn of the channel corresponding to region En of the view Vn.

The coefficient calculator 42c in the present embodiment calculates the weight coefficient for each specific range based on the representative variance value for each specific range.

Specifically, the coefficient calculator 42c calculates the weight coefficient w1 (ω) upon reconstruction of the view V1 based on the representative variance value σT1 and an arbitrarily set parameter. Similarly, the coefficient calculator 42c calculates the weight coefficient wn (ω) upon reconstruction of the view Vn based on the representative variance value σTn and the arbitrarily set parameter. An arbitrarily set parameter can be set for each view. For example, when CT imaging is carried out on sites having many bones, the X-ray amount to be detected decreases due to the absorption of X-rays into the bones. Therefore, in the case of reconstructing the projection data of the view corresponding to the site, the parameter for reducing the influence of the noise is set.

The reconstruction function setting part 42 weights the reference reconstruction function $K_{base}(\omega)$ against the weight coefficient w (ω) for each specific range. In other words, the reconstruction function setting part 42 makes it possible to set the reconstruction function $K_{final}(\omega)$ for each specific range.

Specifically, the reconstruction function setting part 42 weights the reference reconstruction function $K_{base}(\omega)$ using the weight coefficient w1 (ω) of the view V1. Thereby, the reconstruction function setting part 42 sets the reconstruction function $K1_{final}(\omega)$. Similarly, the reconstruction function setting part 42 weights the reference reconstruction function $K_{base}(\omega)$ using the weight coefficient wn (ω) of the view Vn.

Thereby, the reconstruction function setting part 42 sets the reconstruction function $Kn_{final}(\omega)$.

The reconstruction processor 41b can produce a CT image data suitable for each view by reconstructing the data corresponding to each view of the projection data with the set reconstruction function.

<Operation>

Figure 8:
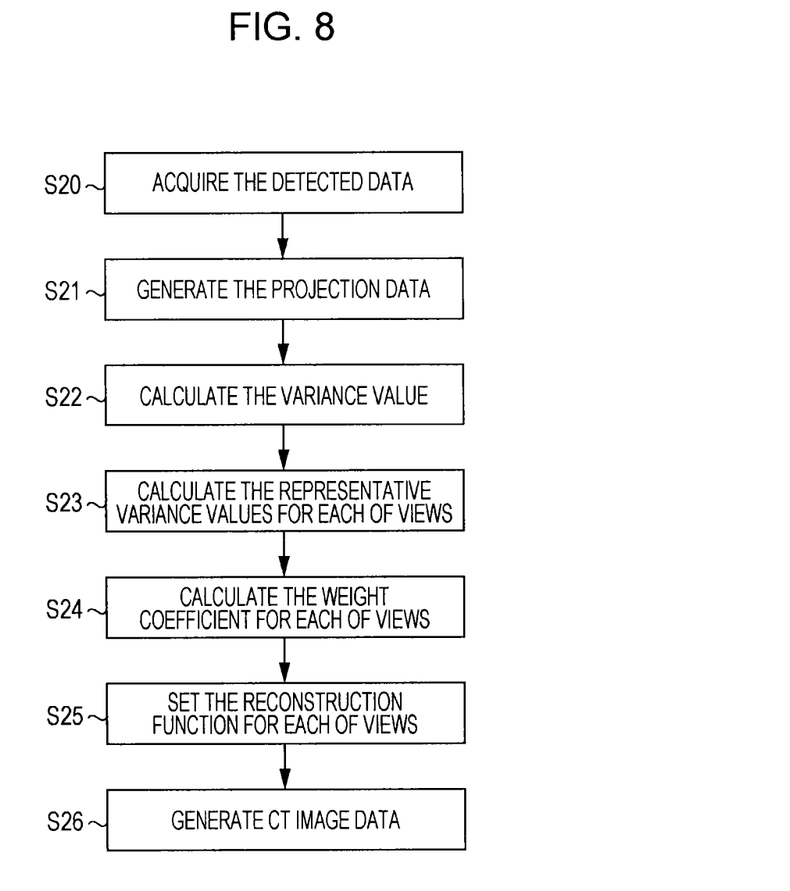
FIG. 8 is a flowchart illustrating the summary of the operation of the X-ray CT apparatus according to the second embodiment.

With reference to FIG. 8, the operation of the X-ray CT apparatus 1 according to the present embodiment will be described.

At first, the X-ray generating part 11 radiates X-rays onto the subject E. The X-ray detector 12 detects the X-rays transmitted through the subject E, and acquires the detected data (S20). The detected data detected by the X-ray detector 12 is collected by the data collector 18. Further, the detected data is transmitted to the processor 41 (preprocessor 41a.)

The preprocessor 41a carries out preprocessing such as logarithmic conversion processing, offset correction, sensitivity correction, and beam hardening correction on the detected data acquired in S20. Thereby, projection data is produced (S21.) The produced projection data is transmitted to the reconstruction processor 41b and the reconstruction function setting part 42 (variance value calculator 42a) based on control through the controller 48.

The variance value calculator 42a divides the projection data produced in S21 for each specific range (here, views V1 to Vn). In addition, the variance value calculator 42a calculates the variance values (the variance values σ1 to σn of the channel) for each specific range (S22.) The calculated variance value σ is transmitted to the representative variance value calculator 42b.

The representative variance value calculator 42b averages the variance values calculated in S22 for each of views V1 to Vn. Thereby, the representative variance value calculator 42b calculates the representative variance values σT1 to σTn for each of views V1 to Vn (S23.) The calculated representative variance values σT1 to σTn are transmitted to the coefficient calculator 42c.

The coefficient calculator 42c calculates the weight coefficients w1 (ω) to wn (ω) based on the representative variance values σT1 to σTn calculated in S23 and the arbitrarily set parameter set for each of views V1 to Vn (S24.)

The reconstruction function setting part 42 sets the reconstruction functions $K1_{final}(\omega)$ to $Kn_{final}(\omega)$ for each of views V1 to Vn using the weight coefficients w1 (ω) to wn (ω) calculated in S24 and the reference reconstruction function $K_{base}(\omega)$ set in advance (S25.) The set reconstruction functions $K1_{final}(\omega)$ to $Kn_{final}(\omega)$ are transmitted to the reconstruction processor 41b.

The reconstruction processor 41b convolves the projection data with the reconstruction functions $K1_{final}(\omega)$ to $Kn_{final}(\omega)$ for each of views V1 to Vn set in S25 and back-projecting this projection data. Thereby, the reconstruction processor 41b produces a CT image data (S26.). The display controller 43 can display the CT image based on the produced CT image data on the display 45. This CT image is produced for each specific range (the view, a site of the subject E, etc.) using the optimum reconstruction function. Accordingly, it is possible to obtain a desired CT image such as an image having a good S/N, an image having good granularity, etc. for each specific range.

<Operation and Effect>

The operation and effect of the present embodiment will be described.

The variance value calculator 42a in the present embodiment divides the projection data for each specific range (for example, views V1 to Vn). In addition, the variance value calculator 42a calculates the variance values (σ1 to σn) for each specific range. The representative variance value calculator 42b weights the reference reconstruction function set in advance based on statistics representing statistical dispersion of the X-ray amount for each specific range (for example, views V1 to Vn). Thereby, the reconstruction function setting part 42 sets the reconstruction function used for reconstruction. For example, the reconstruction function setting part 42 calculates the representative variance values σT1 to σTn for each specific range based on the variance value of the X-ray amount of the detected X-rays. The coefficient calculator 42c calculates the weight coefficients w1 (ω) to wn (ω) for each specific range based on the representative variance value for each specific range. The reconstruction function setting part 42 weights the reference reconstruction function $K_{base}(\omega)$ using the weight coefficient for each specific range, and thereby, sets the reconstruction function $K_{final}(\omega)$ for each specific range.

Thus, the reconstruction function setting part 42 weights the reference reconstruction function $K_{base}(\omega)$ using the weight coefficients w1 (ω) to wn (ω) for each specific range, and thereby, sets the optimum reconstruction functions $K1_{final}(\omega)$ to $Kn_{final}(\omega)$ for each specific range. For example, assuming that the view V1 is the projection data of a site having many bones, the X-ray amount to be detected in the range of the view V1 is smaller. Accordingly, the coefficient calculator 42c calculates a weight coefficient w1 (ω) in which weighting on the part with a high spatial frequency is smaller than the reference reconstruction function $K_{base}(\omega)$ based on the representative variance value σT1. The reconstruction processor 41b reconstructs the view V1 using the reconstruction function $K1_{final}(\omega)$ set based on the weight coefficient w1 (ω). Therefore, the CT image data corresponding to the projection data of the view V1 obtained by reconstruction is an image having a good S/N with the noise reduced. In other words, the X-ray CT apparatus 1 of the present embodiment makes it possible to set the reconstruction function for obtaining a desired image for each range.

Common Effect(s) in the Embodiment(s)

According to the X-ray CT apparatus of at least one of the above-described embodiments, the coefficient calculator serves to calculate the weight coefficient according to statistics of the projection data. Statistics include, for example, a variance value (representative variance value) or the standard deviation (representative standard deviation). Then, the reconstruction function setting part sets the reconstruction function by weighting the reference reconstruction function using the calculated weight coefficient. In other words, the X-ray CT apparatus 1 of the present embodiment makes it possible to set the reconstruction function for obtaining a desired image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
   an X-ray source configured to generate X-rays while rotating along a circuital orbit around a subject;
   an X-ray detector having a plurality of channels and configured to detect the X-rays transmitted through the subject in each channel;
   a reconstruction function setting part configured to set the reconstruction function by weighting a predetermined reference reconstruction function based on statistics representing a statistical dispersion of an X-ray amount of the detected X-rays; and
   a reconstruction processor configured to carry out reconstruction of projection data generated from the detected X-rays, based on the reconstruction function to produce image data.

2. The X-ray CT apparatus according to claim 1, wherein the reconstruction function setting part further comprises:
   a statistics calculator configured to calculate the statistics based on the X-ray amount detected for each channel of the X-ray detector regarding the projection data;
   a representative statistics calculator configured to calculate representative statistics based on the plurality of calculated statistics; and
   a coefficient calculator configured to calculate a weight coefficient based on the representative statistics,
   wherein the reconstruction function setting part sets the reconstruction function by weighting the reference reconstruction function with the weight coefficient.

3. The X-ray CT apparatus according to claim 2, wherein the representative statistics calculator calculates the representative statistics based on all statistics calculated by the statistics calculator.

4. The X-ray CT apparatus according to claim 2, wherein the statistics calculator divides the projection data for each specific range of a plurality of specific ranges and calculates the statistics for each specific range,
   the representative statistics calculator calculates the representative statistics for each specific range based on the statistics for each specific range,
   the coefficient calculator calculates the weight coefficient for each specific range based on the representative statistics for each specific range, and
   the reconstruction function setting part sets the reconstruction function for each specific range by weighting the reference reconstruction function with the weight coefficient for each specific range.

5. The X-ray CT apparatus according to claim 4, wherein the specific range comprises a single rotation from one view of the circuital orbit of the X-ray source.

6. The X-ray CT apparatus according to claim 4, wherein the specific range is a region corresponding to a range of the X-ray detector in which, when the X-rays are radiated onto the subject from an arbitrary position in the circuital orbit, the X-rays are detected.

7. The X-ray CT apparatus according to claim 4, wherein the specific range is a site of the subject.

* * * * *